US006860876B2

United States Patent
Chen

(12) United States Patent
(10) Patent No.: US 6,860,876 B2
(45) Date of Patent: Mar. 1, 2005

(54) VERSATILE INTERVENTIONAL CORONARY GUIDING CATHETER

(76) Inventor: Jack P. Chen, 720 Aran Dr., Roswell, GA (US) 30076

( * ) Notice: Subject to any disclaimer, the term of this patent is extended or adjusted under 35 U.S.C. 154(b) by 0 days.

(21) Appl. No.: 10/434,545

(22) Filed: May 9, 2003

(65) Prior Publication Data
US 2004/0225297 A1 Nov. 11, 2004

(51) Int. Cl.[7] .............................................. A61M 25/01
(52) U.S. Cl. ................. 604/528; 604/534; 604/508; 604/510
(58) Field of Search ..................... 606/108; 600/435; 604/523, 528, 532–535, 508, 510, 103.04, 103.05, 164.08, 171

(56) References Cited

U.S. PATENT DOCUMENTS

| 5,098,412 A | 3/1992 | Shiu |
| 5,540,659 A * | 7/1996 | Teirstein ................ 604/104 |
| 2003/0109852 A1 | 6/2003 | Peterson et al. |
| 2003/0130598 A1 | 7/2003 | Manning et al. |

* cited by examiner

Primary Examiner—Nicholas D. Lucchesi
Assistant Examiner—Kevin C. Sirmons
(74) Attorney, Agent, or Firm—Sutherland Asbill & Brennan LLP

(57) ABSTRACT

A versatile coronary guiding catheter device and methods of use are provided. The device includes a guiding catheter, an anchor shaft, and a sleeve. In one embodiment, the anchor shaft can be moved relative to the catheter body to form a loop defined by the portions of the anchor shaft and catheter body that are between the distal end of the sleeve and a hinge point. The loop engages an interior surface of the aorta in manner effective to facilitate insertion of the distal end of the catheter body into a coronary ostium, to provide backup support for maintaining a position of the distal end of the catheter body within a coronary ostium, or both. The sleeve may also be moveable to increase the control of the loop size and position, to facilitate greater control of the placement of the catheter tip.

23 Claims, 11 Drawing Sheets

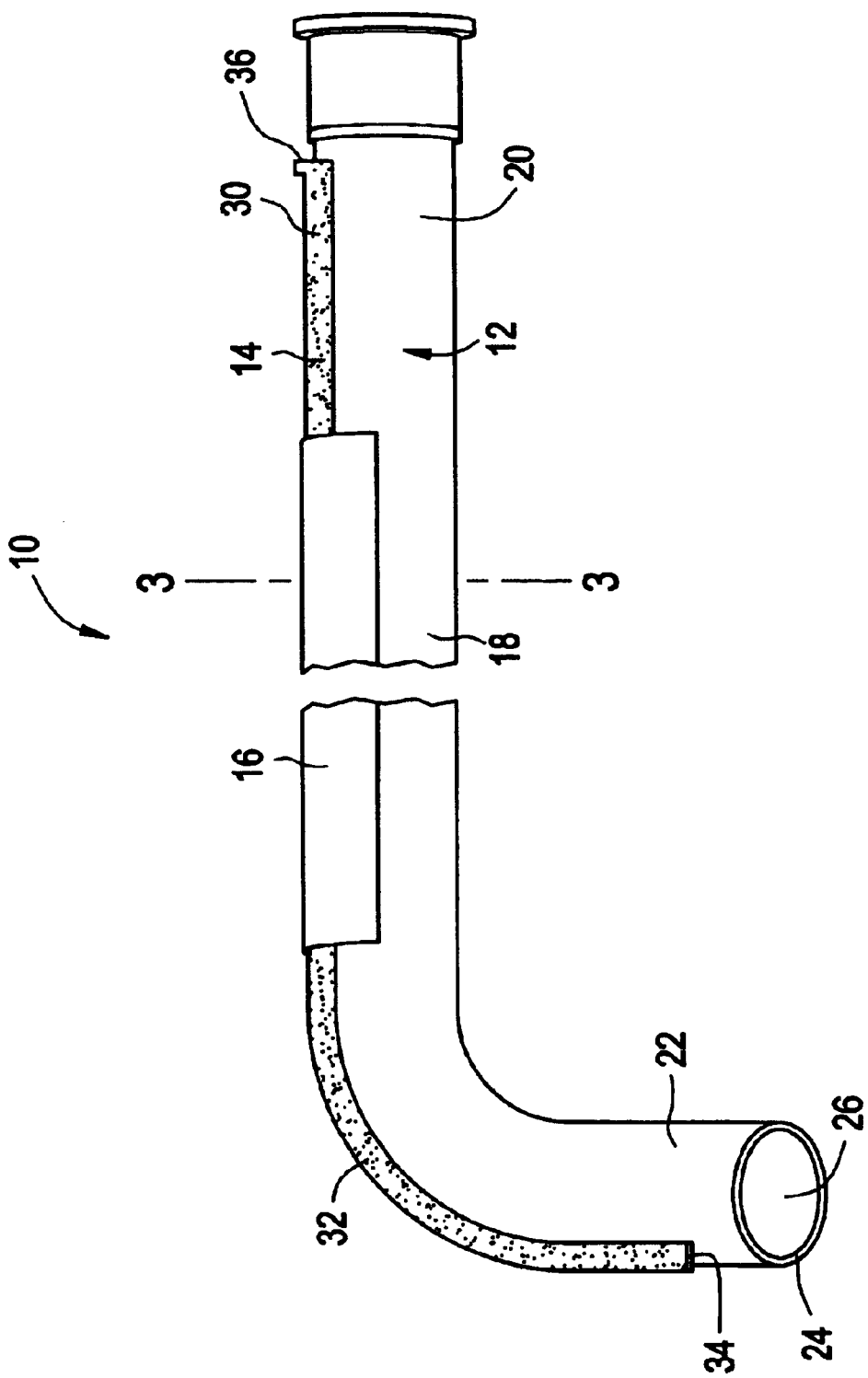

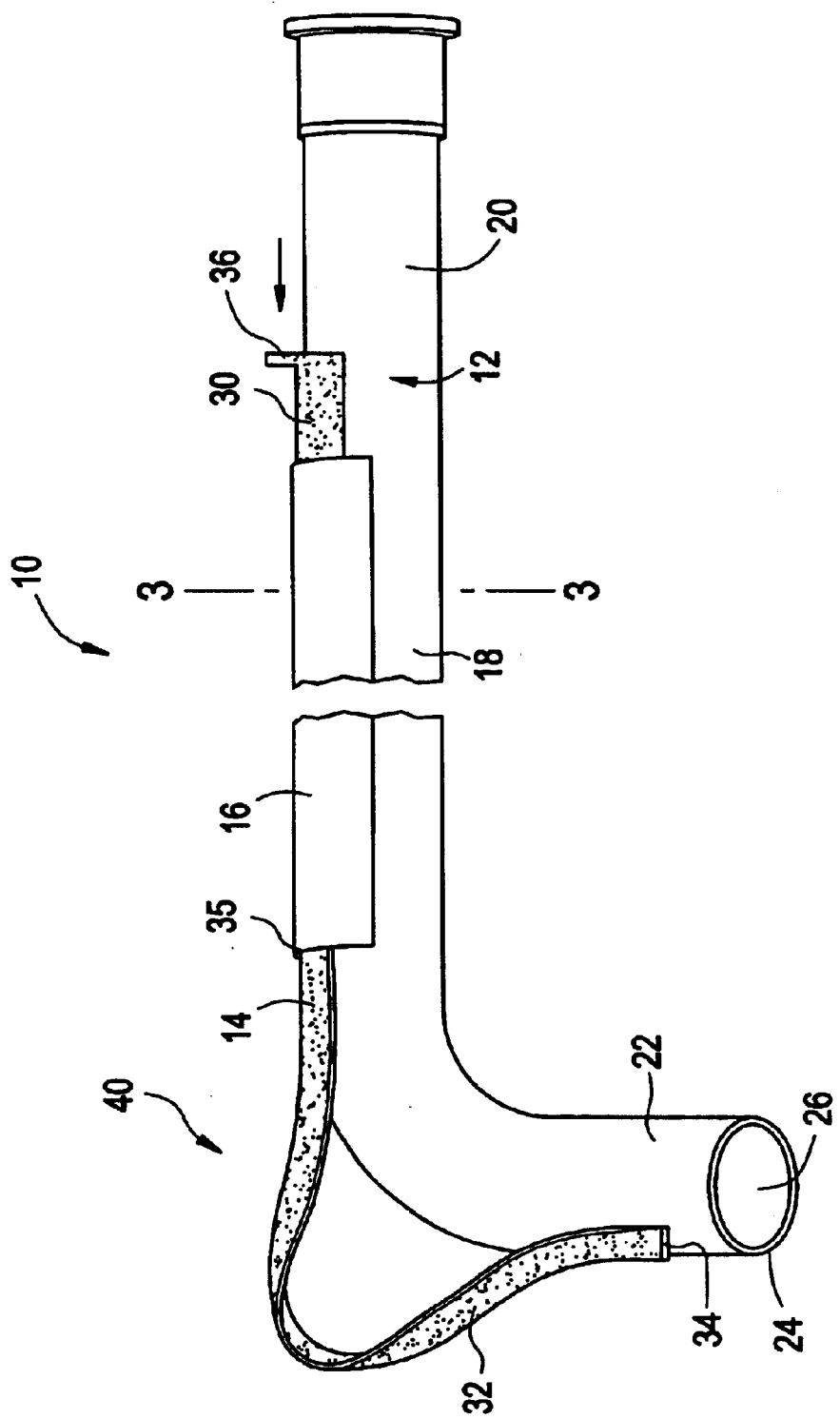

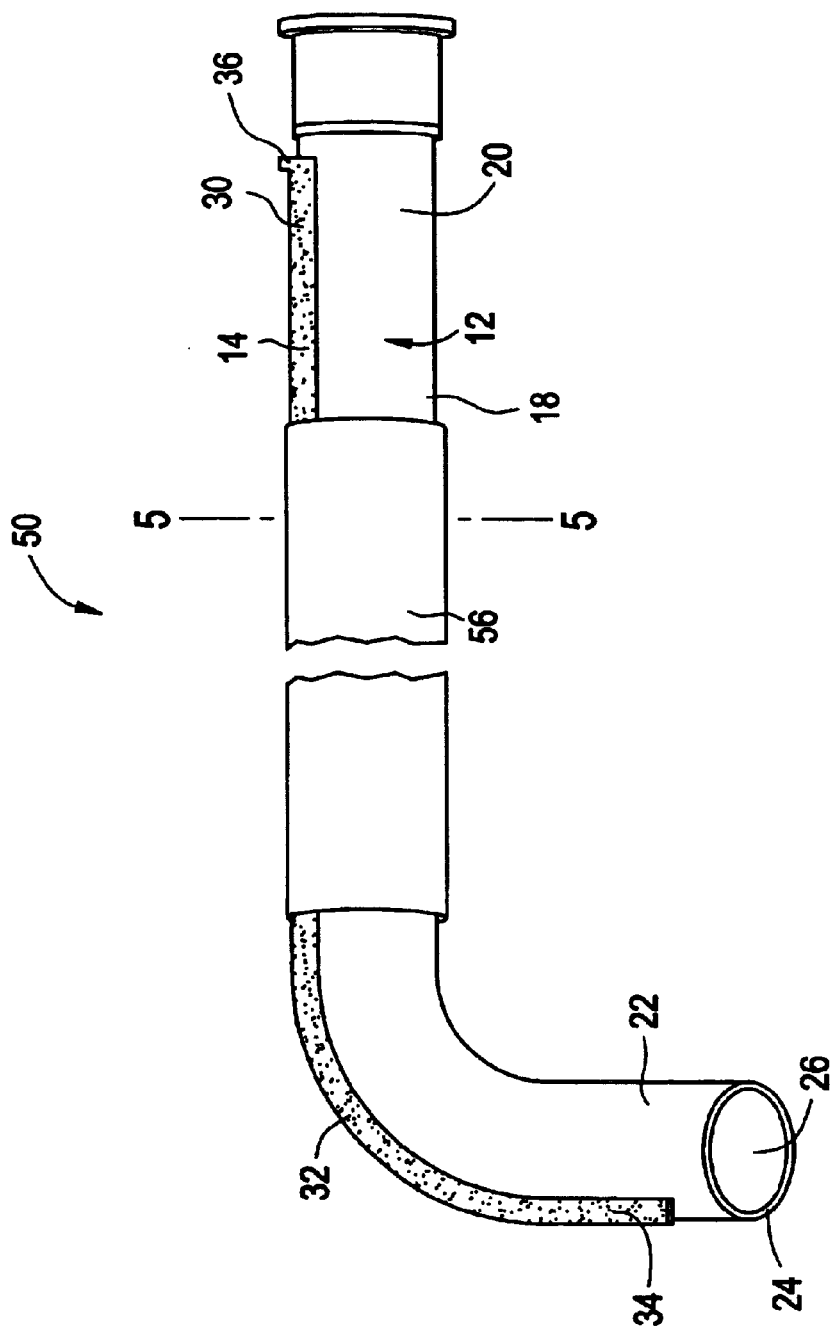

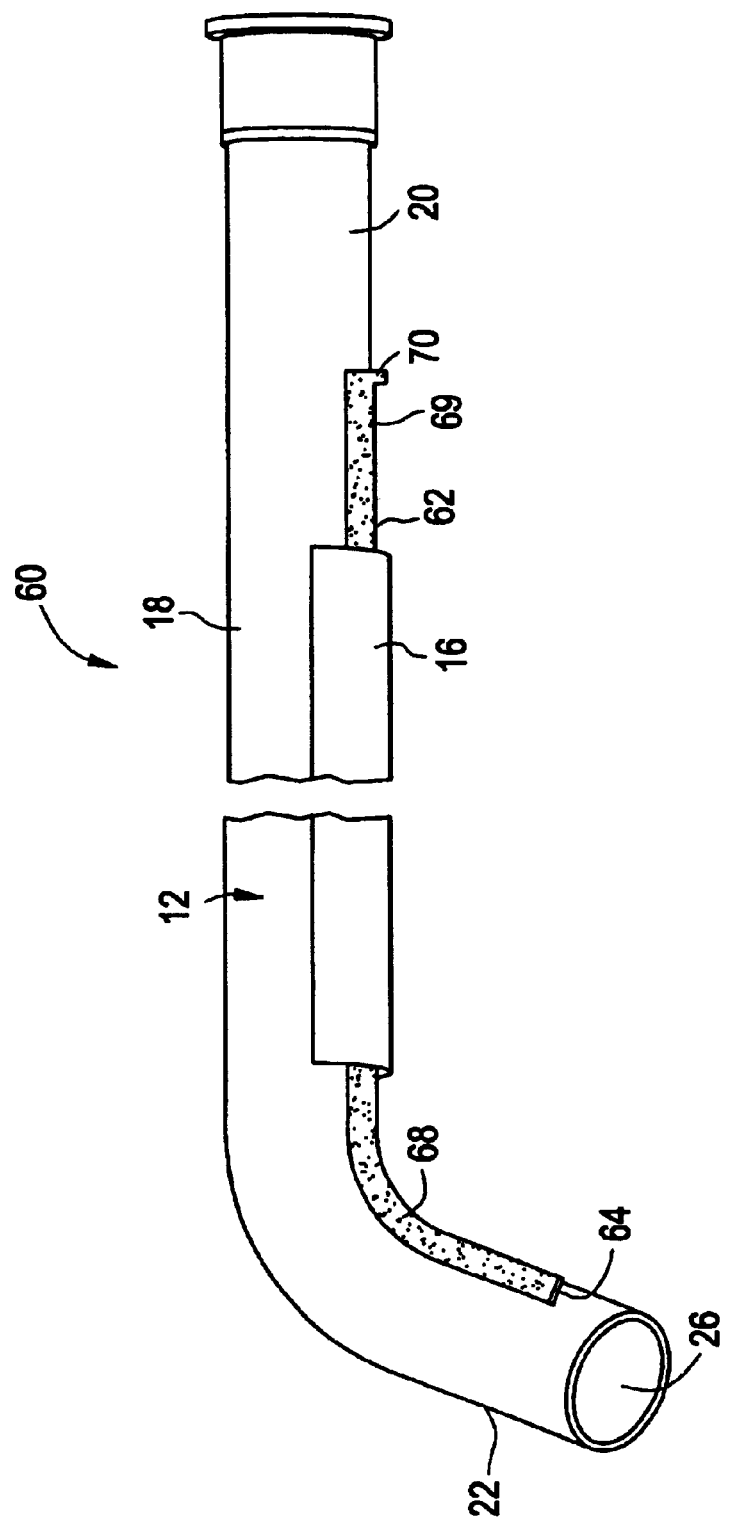

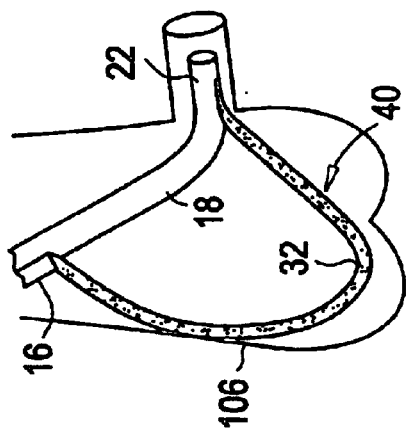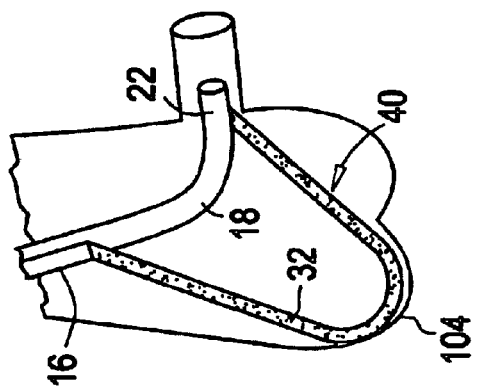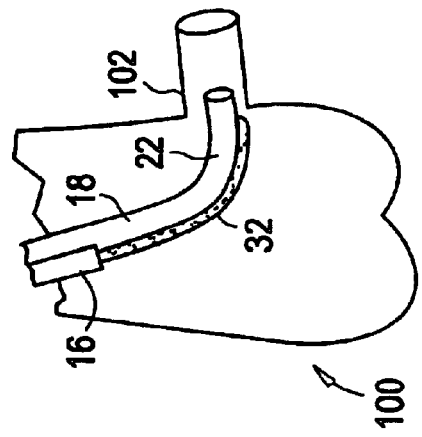

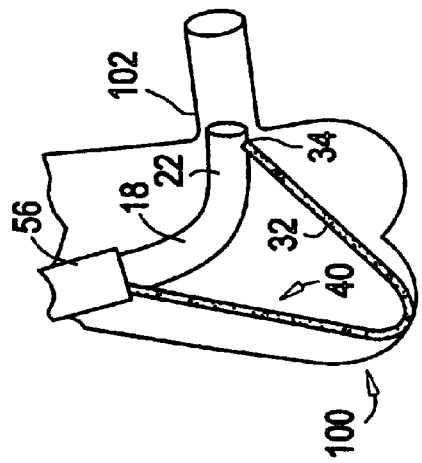
FIG. 9A
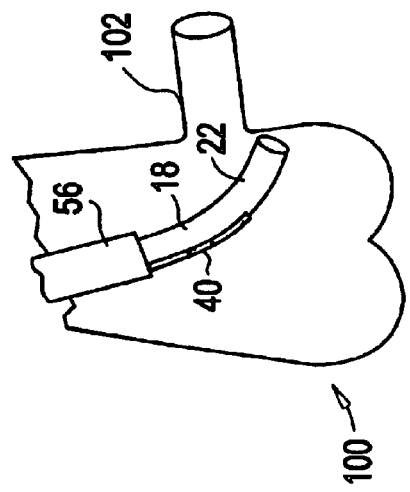
FIG. 9B
FIG. 9C

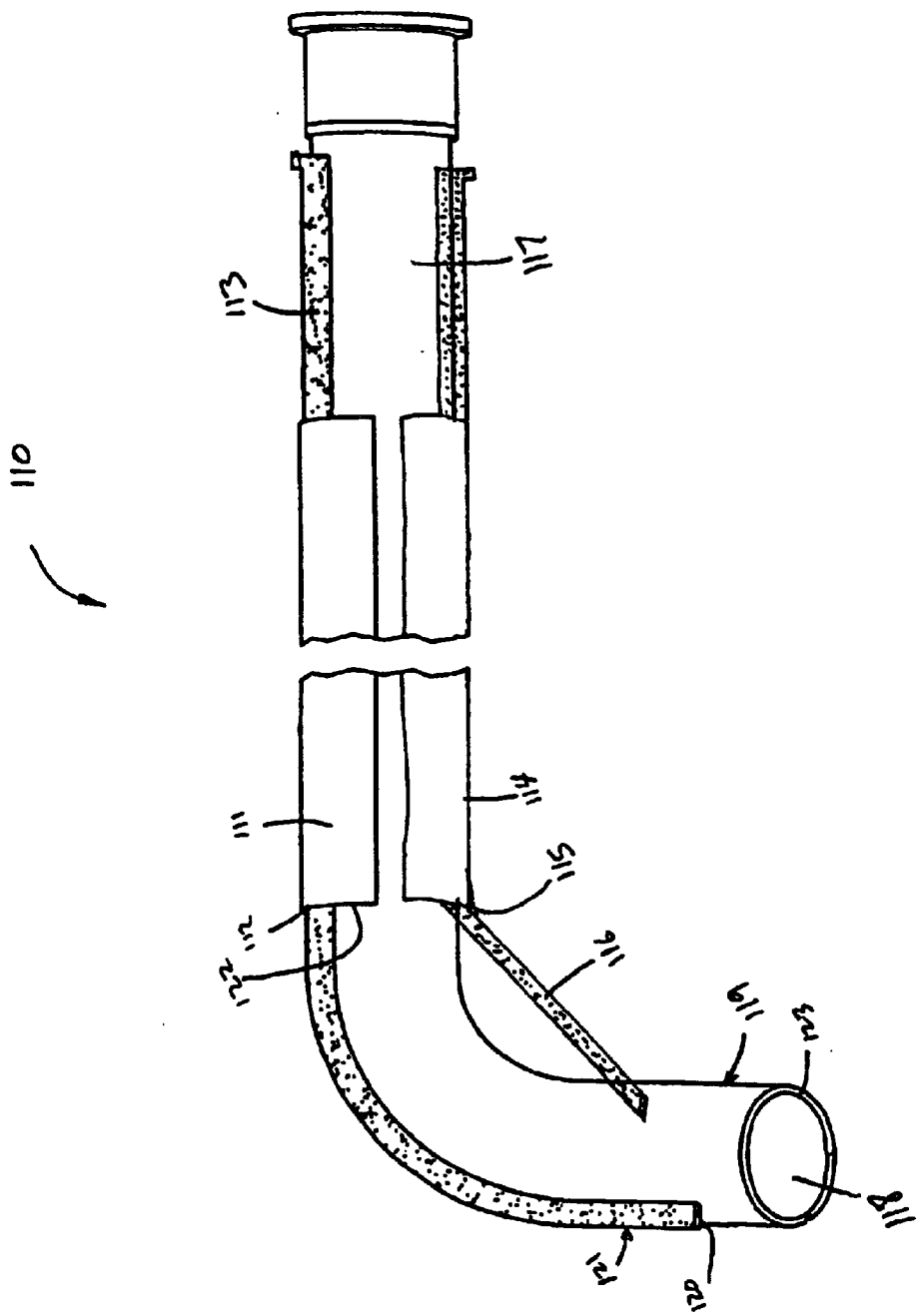

VERSATILE INTERVENTIONAL CORONARY GUIDING CATHETER

BACKGROUND OF THE INVENTION

This invention is generally in the field of medical devices, and more particularly catheters for use in interventional cardiology.

Catheters are often used in the performance of medical procedures such as coronary angiography for injecting dye, or the like, into the cardiovascular system for diagnosis; and angioplasty to widen the lumen of a coronary artery which has become at least partially blocked by a stenotic lesion causing an abnormal narrowing of the artery due to injury or disease.

Interventional cardiology is a medical subspecialty in which a guiding catheter is used to insert balloons, stents, and other therapeutic devices (e.g., laser catheters, atherectomy catheters) into arteries supplying blood to the heart muscle, i.e., coronary arteries, to open fatty blockages, e.g., percutaneous transluminal coronary angioplasty. These devices move through an axial lumen in the catheter. Generally, a catheter is inserted into an artery in the groin or wrist of the patient and advanced into the aorta. The tip, or distal end, of the catheter then is inserted into the ostium (the opening) of a coronary artery, one of three small vessels branching off the aortic root (the base of the aorta) around the heart. The opposite, or proximal, end of the guiding catheter, through which balloons stents or other devices are introduced and advanced into the lumen of the guiding catheter, remains outside of the patient's body. The balloon or other device is advanced through the lumen of the catheter, out an aperture in the tip, and into the coronary artery to the blockage.

Varying degrees of resistance to balloon advancement are encountered, depending upon several factors, such as tortuosity, calcification (or stiffness), and size of the coronary artery. This resistance translates into an equal and opposite force onto the guiding catheter, which undesirably tends to back the guiding catheter out of the coronary ostium. The force or support with which a particular catheter can exert to oppose this retreat and maintain the position of the tip within the vessel ostium determines the catheter's ability to allow passage of balloons or other devices, for a successful interventional procedure.

There are varying catheter design approaches for dealing with this advancement resistance. For example, a catheter design may be based upon the curvature of the catheter tip, as well as on the thickness and stiffness of the wall of the catheter. "Aggressive" catheter designs, such as Amplaz or Voda type, provide for "deep seating" of the tip further into the vessel and afford greater maintenance of tip position "backup support" while advancing the balloon. The disadvantage of these catheters, however, is an increased risk of vessel trauma or dissection, as the tip is forcefully engaged in the vessel ostium. Conversely, "conservative" catheter designs, such as Judkins, are more flexible and insert only minimally, atraumatically, into the coronary ostium. The drawback of this design, however, is that it offers less backup support and consequently increases the potential failure to deliver the balloon or other device to the target blockage. In addition to backup support, the locations of the coronary arteries are extremely variable among patients, necessitating multiple curvature designs to accommodate the wide array of anatomical variations.

Therefore, the selection of catheter is a critical part of an interventional procedure. Oftentimes, multiple different catheters need to be tried before an appropriate one is identified. Such multiple catheter exchanges can jeopardize patient safety, frustrate the physician, increase the cost of the procedure, and increase the cost of providing the inventory of catheters. At times, the physician may have to accept a suboptimal result because a superior, but bulkier, device such as a stent is not deliverable without adequate guiding catheter backup support. It would be desirable to take some of the "guesswork" out of guiding catheter selection, both for considerations of backup support as well as anatomic variations. It would be desirable to provide a single, versatile catheter, combining favorably features of aggressive designs and conservative designs as needed.

U.S. Pat. No. 5,098,412 to Shiu discloses a support system for a guiding catheter. The catheter comprises a main lumen and a secondary lumen, which are connected integrally together throughout the proximal portion of the length of the catheter but are separated throughout a distal portion. An incompressible, flexible, elongate element is slidably disposed within the secondary lumen and is anchored at the distal end of the catheter. The proximal end of the catheter includes operating means to exert an endwise force on the elongate element to cause the separated portion of the secondary lumen to move away from the main lumen to brace the catheter against opposite walls of the aorta for "backup" support and to retain it in a selected position. This design, however, requires two full lumens, each having its own wall structure all the way around the lumen perimeter. This feature results in a double layer of sleeve material where the sleeves of the two lumens interface, adding thickness to the catheter device, causing it to have a larger profile without a corresponding increase in lumen diameter, even though it is highly desirable to maximize the ratio of the inside diameter of any functional lumen to the outside diameter of the tubular body in coronary arterial applications. That is, for a given lumen diameter sized to accommodate a particular balloon or other therapeutic device, the catheter desirably has as small a profile, or sheath size, as possible in order to minimize arterial trauma (e.g., trauma to the femoral artery). In another aspect, it would be desirable to provide means for more finely controlling the position of the backup support member, the position of the distal tip of the primary catheter, or both, in order to enhance the versatility of a single catheter design.

SUMMARY OF THE INVENTION

Versatile guiding catheter devices and methods of use are provided.

In one aspect, the device includes an extension catheter. For example, in a preferred embodiment, the device includes (i) an elongated, flexible, tubular catheter body having a proximal end, a distal end, and a central lumen extending therebetween; (ii) an elongated, flexible sleeve having a proximal end and a distal end, the sleeve being secured to and covering at least a portion of the outer, greater curvature of the catheter body so as to define a secondary lumen between the sleeve and an outer surface area of the catheter body, and the distal end of the sleeve being in a position proximal the distal end of the catheter body; and (iii) an anchor shaft having a proximal end and a distal end, the anchor shaft extending through the secondary lumen, the distal end being fixedly attached to the catheter body at an outer surface area between the distal end of the catheter body and the distal end of the sleeve to form a hinge point about which the distal portion of the anchor shaft can rotate with respect to the catheter body, wherein the proximal end of the anchor shaft can be reversibly advanced (preferably manually) toward the distal ends of the anchor shaft and catheter body to cause the distal end portion of the anchor shaft to bow away from the catheter body in the region between the hinge point and the distal end of the sleeve, forming a loop which is defined by the portions of the anchor shaft and catheter body that are between the distal end of the sleeve and the hinge point.

In another aspect, the guiding catheter device includes a retraction anchor shaft, alone or in combination with the extension anchor shaft described above. In a preferred embodiment, the versatile guiding catheter device includes (i) a catheter body as described above; (ii) a sleeve and secondary lumen as described above, except attached at the inner, lesser curvature of the catheter body; and (iii) an anchor shaft and hinge point as described above, but which is adapted so that the proximal end of the anchor shaft can be reversibly retracted (preferably manually) away from the sleeve to cause the distal end of the anchor shaft to move toward the sleeve, decreasing the radius of curvature of the distal end portion of the catheter body that is between the distal end of the sleeve and the hinge point.

In one embodiment of the device with either a retraction or extension anchor shaft, the sleeve is moveably secured to the catheter body, so that the sleeve can be reversibly advanced (preferably manually) toward the proximal ends of the anchor shaft and catheter body. In a variation of this embodiment, the proximal end portion of the moveable sleeve comprises a locking means for securing the sleeve in one or more positions along the catheter body.

Optionally, the proximal end portion of the anchor shaft, either extension or retraction, comprises a locking means for securing the anchor shaft at one or more positions along the catheter body.

The distal end portion of the catheter body is curved. For the extension anchor shaft, the hinge point preferably is located on the outer curvature of the curved distal end portion of the catheter body. For the retraction anchor shaft, the hinge point preferably is located on the inner curvature of the curved distal end portion of the catheter body.

In yet another aspect, methods are provided for using these versatile guiding catheter devices to accurately guide a catheter into a coronary artery for coronary intervention. The methods comprise inserting into the aorta of a patient in need of coronary intervention the distal ends of the catheter body, sleeve, and anchor shaft, with the distal end portion of the anchor shaft in a resting position adjacent the catheter body.

For the extension anchor shaft, the method further includes advancing (preferably manually) the proximal end of the anchor shaft toward the distal ends of the anchor shaft and catheter body to cause the distal end portion of the anchor shaft to bow away from the catheter body in the region between the hinge point and the distal end of the sleeve, forming a loop which is defined by the portions of the anchor shaft and catheter body that are between the distal end of the sleeve and the hinge point, and then adjusting the position of the proximal end of the anchor shaft to cause the loop to engage the opposing wall in the interior surface of the aorta in manner effective to facilitate insertion of the distal end of the catheter body into a coronary ostium, to provide backup support for maintaining a position of the distal end of the catheter body within a coronary ostium, or both. For the retraction anchor shaft, the method further includes retracting the proximal end of the anchor shaft away from the sleeve to cause the distal end of the anchor shaft to move toward the sleeve, decreasing the radius of curvature of the distal end portion of the catheter body that is between the distal end of the sleeve and the hinge point, and then adjusting the position of the proximal end of the anchor shaft to facilitate insertion of the distal end of the catheter body into a coronary ostium. If the sleeve is moveable, then the method can further include retracting the sleeve toward the proximal ends of the anchor shaft and catheter body to enlarge the loop or fine-tune the radius of curvature of the distal end portion of the catheter body.

BRIEF DESCRIPTION OF THE DRAWINGS

FIG. 1 is a perspective view of one embodiment of a catheter device with an extension anchor shaft in a resting position.

FIG. 2 is a perspective view of the catheter device of FIG. 1 with the anchor shaft in an extended position.

FIG. 4 is a perspective view of one embodiment of a catheter device with an extension anchor shaft in a resting position and with a moveable sleeve.

FIG. 6 is a perspective view of one embodiment of a catheter device with a retraction anchor shaft in a resting position.

FIGS. 8A–C illustrate use of one embodiment of a catheter device with an extension anchor shaft, shown located for use within an aorta in a resting position (FIG. 8A), in a mid-extension position (FIG. 8B), and in a full-extension position (FIG. 8C).

FIGS. 9A–C illustrate use of one embodiment of a catheter device with an extension anchor shaft and moveable sleeve. FIG. 9A depicts a resting configuration with suboptimal fitting of an unusual coronary location shown with the moveable sleeve in a distal position, and FIGS. 9B–C illustrate progressive distal extension of the anchor shaft with simultaneous proximal retraction of the moveable sleeve for optimal coronary engagement.

FIGS. 11A–C depict cross-sectional side views, and FIG. 11D depicts a top view of the anchor shaft shown in FIGS. 11B–C.

FIG. 12 is a perspective view of one embodiment of a guiding catheter device with both an extension anchor shaft and a retraction anchor shaft.

DETAILED DESCRIPTION OF THE INVENTION

An improved, versatile coronary guiding catheter device has been developed. Advantageously, the catheter device described herein can reduce the criticality of guider selection, as the catheter is versatile and adaptable to a variety of arterial sizes and shapes. It can beneficially reduce or eliminate the need for awkward and potentially dangerous mid-procedure exchanges of the guiding catheter.

The catheter device includes a guiding catheter, an anchor shaft, and a sleeve. Advantageously, the present device enables the catheter design to have relatively thinner wall structure, compared to conventional catheter designs, because the stiffness of the catheter body becomes less critical due to backup support being provided by the anchor shaft. In addition, the present catheter device advantageously removes some of the guesswork out of the selection of the guiding catheter, both for considerations of backup support and anatomic variations. The resistance to advancement of hardware (e.g., balloons, stents, or atherectomy devices) into the coronary artery, and hence need for "aggressive" guide catheter engagement, often cannot be predicted a priori during initial catheter selection at the beginning of an interventional procedure. The dynamic nature of the present catheter design allows for fine-tuning of the degree of ostial engagement (with its attendant potential for arterial trauma or dissection) as hardware is simultaneously advanced into the coronary. In addition, the duration of deep catheter engagement advantageously is minimized, as the catheter can assume resting position during most of the procedure (i.e., before and after actual hardware advancement, in contrast to a static aggressive catheter, with prolonged arterial trauma throughout the duration of the entire procedure. Instead of having to choose the perfect catheter for a particular patient and situation, the present catheter device can be readily adapted to the situation during the procedure.

The catheter device can be further understood with reference to the exemplary embodiments illustrated in FIGS. 1–10.

Figure 3:
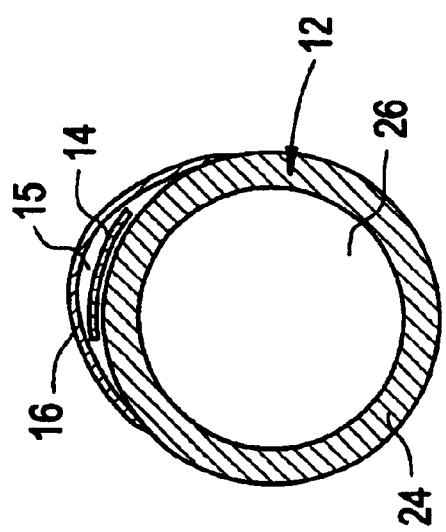
FIG. 3 is a cross-sectional view of the midsection of the catheter device of FIGS. 1 and 2.

A preferred embodiment of the versatile catheter device is illustrated FIGS. 1–3. The catheter device 10 includes a guiding catheter 12, an anchor shaft 14, and a sleeve 16. In this embodiment, the anchor shaft may be referred to herein as an extension anchor shaft, because the physician holding the proximal end of the anchor shaft extends it distally from its resting position in order to engage its support function. The guiding catheter 12 comprises an elongated, flexible, tubular catheter body 18 having a proximal end, a distal end, and a central lumen extending therebetween. The catheter body includes a distal end portion 22 extending from the distal (tip) end of the catheter body to a location spaced proximally from the tip and a proximal end portion 20 extending proximally from the proximal end of the distal end portion. The distal end portion 22 preferably is variably curved. The catheter body 18 includes a wall structure 24 defining the central lumen 26. The catheter body 18 is formed by conventional means from biologically compatible synthetic polymers.

In a preferred embodiment, the anchor shaft 14 comprises an elongated, incompressible, semi-rigid ribbon, which approximately spans the length of the guiding catheter body 18, adjacent the outer surface of and substantially parallel to the catheter body. The anchor shaft 14 has a proximal end portion 30 and a distal end portion 32, which is attached to the outer surface of the catheter body 18 at a position proximal a short distance (e.g., between about 1 and about 5 cm) from the tip of the catheter body. The area at which the anchor shaft is attached to the guiding catheter is referred to herein as the "hinge point" 34, because the anchor shaft and guiding catheter can at least partially move, e.g., rotate, relative to each other about this point. The anchor shaft is formed by conventional means from biologically compatible synthetic polymers, metals, or a combination thereof. The anchor shaft preferably is made of a semi-soft material (e.g., TEFLON™) and preferably has a width between about 20% and about 25% of the circumference of the catheter body 18.

Figure 11A:
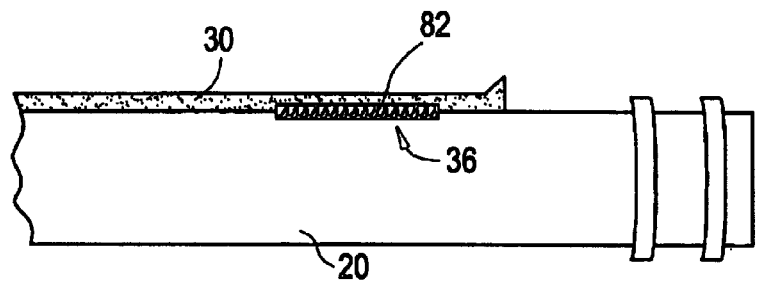
FIGS. 11A–D illustrate various non-limiting embodiments of locking mechanisms for securing the anchor shaft position along the catheter body.
Figure 11B:
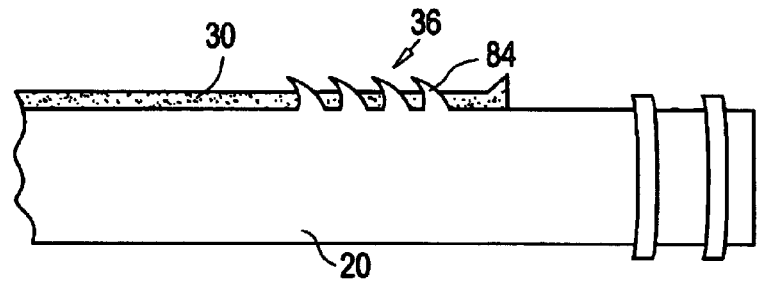
Figure 11C:
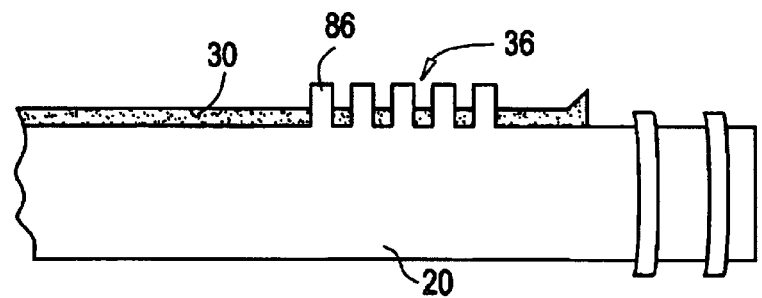
Figure 11D:
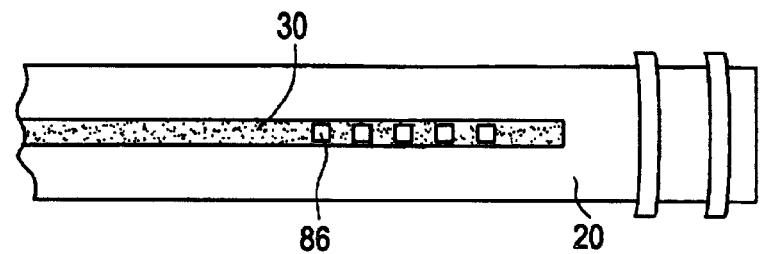

In a preferred embodiment, the sleeve 16 is a thin, elongated, flexible covering over at least a portion of the catheter body 18, forming a secondary lumen 15 between the sleeve 16 and a longitudinal area along the outer surface of wall 24 of the catheter body 18. See FIG. 3. The sleeve 16 extends from near the proximal end of the catheter body 18 and terminates a short distance proximal the hinge point 34. The anchor shaft 14 is slidably positioned in the secondary lumen 15. The proximal end of the anchor shaft extends proximally beyond the proximal end of the sleeve and terminating into or at an anchor locking means 36, which secures the adjusted position of the anchor shaft 14 relative to the catheter body 18. The sleeve 16 can be very thin and made of essentially any flexible material; it need only be strong enough to contain outward forces exerted by extension of the anchor shaft to separate the sleeve from the catheter body. The sleeve 16 preferably is formed by conventional means from biologically compatible synthetic polymers. It may be formed integrally with the catheter body, or formed separately and then attached thereto. The optional locking means could be essentially any type of mechanism for securing the anchor shaft position relative to the catheter body position. For instance, the locking means could include one or more of the following non-limiting examples: hook-and-loop fasteners such as VELCRO™, notch mechanisms, button-hole mechanisms, releasably attachable pressure sensitive adhesive materials, snaps, clips, clamps and combinations thereof. See, for example, FIGS. 11A–D, which illustrate some possible embodiments of such locking means. FIG. 11A shows proximal end 20 of catheter body with proximal end 30 of anchor shaft secured together with locking means 36, which is in the form of a hook-and-loop fastener 82, which would typically consist of a hook (or loop) portion fixed onto an outer surface of the proximal end 20 and a loop (or hook) portion fixed onto an interfacing portion of the proximal end 30. FIG. 11B illustrates locking means 36, which is in the form of notches 84 designed to secure the anchor shaft at variable positions along the catheter body. FIG. 11C illustrates locking means 36, which is in the form of buttons/holes 86 designed to secure the anchor shaft at variable positions along the catheter body. FIG. 11D is a top view of FIGS. 11B and 11C, and shows the fenestrated proximal anchor shaft which comprises part of locking means 36. Five fenestrations (e.g., button holes) are shown within the width of the anchor shaft; however, more or less than five fenestrations (e.g., 3, 4, 6, etc.) could be employed.

In operation, the anchor locking means 36 is disengaged and then the proximal end portion 30 of the anchor shaft 14 is advanced distally along the secondary lumen 15 defined between the sleeve 16 and a longitudinal area along the outer surface of wall 24 of the catheter body 18. This advancement causes the distal end portion 32 of the anchor shaft 14, as it exits from the secondary lumen 15, to bow or flex away from the catheter body 18 in the region between the hinge point 34 and the distal end 35 of the sleeve, forming a loop 40, which is defined by the distal portion of the anchor shaft that is distal the distal end of the secondary lumen, and the distal portion of the catheter body that is distal the distal end of the secondary lumen. See FIG. 2.

The size or diameter of this loop 40 is controlled by the advancement or retraction of the anchor shaft 14 relative to the catheter body 18. The loop size or diameter determines the degree of backup support provided during use, e.g., coronary intervention. See FIGS. 8A–C, which shows this embodiment positioned within aorta 100 with distal end of catheter body being directed into the coronary ostium 102. The catheter tip can be forced into the coronary ostium as the loop size is enlarged. As the loop is enlarged, it can sequentially abut the contralateral cusp 104 (e.g., a mid- or moderate-extension position—FIG. 8B, like an EBU- or XB-type catheter), offering moderate support, and then abut the contralateral wall 106 (e.g., a full-extension position—FIG. 8C, like an Amplatz- or Voda-type catheter), offering greater support. In this way, a single design catheter device can be used to successfully negotiate a relatively narrow or relatively wide aortic root diameter with equal precision, because the anchor shaft position can be adjusted to conform the catheter as needed to fit a variety of coronary locations and aortic root widths.

The guiding catheter devices described herein allow for universal application to virtually all coronary interventions. With the anchor shaft retracted, the device assumes a conservative or zero (i.e., initial resting) configuration, which approximates the design of a Judkins catheter. As the anchor shaft is progressively advanced, if and as needed, gradually increasing degrees of backup support are at the physician's disposal via anchor shaft advancement and transformation into the extended configurations. For example, in an intermediate embodiment, the curve of the distal portion of the catheter body resembles that of an EBU or XB catheter (for contralateral cusp abutment). In another example, in a fully extended or aggressive configuration, the curve of the distal portion of the catheter body resembles that of an Amplatz- or Voda-like support (for contralateral wall abutment).

Figure 5:
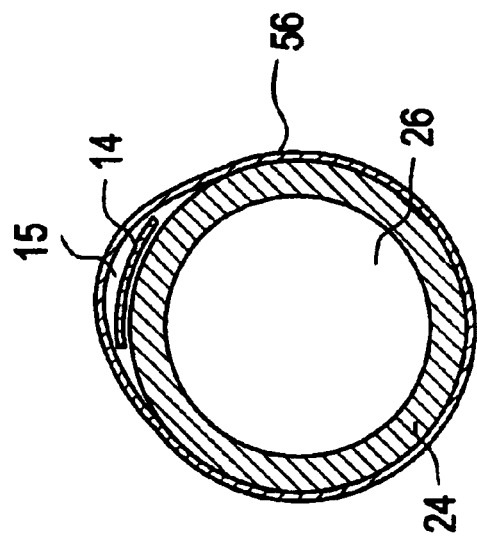
FIG. 5 is a cross-sectional view of the midsection of the catheter device of FIG. 4.

The sleeve may also be moveable to increase the control of the loop size and position, to facilitate greater control of the placement of the catheter tip. FIGS. 4, 5 and 9 illustrate one such catheter device. It includes a moveable sleeve, which can be advanced or retracted along the catheter body to provide additional operational versatility. This feature allows the physician to further vary the size of the loop, as well as its position along the catheter body, to fine tune the orientation and backup support for the distal tip of the catheter.

As shown in FIGS. 4 and 5, catheter device 50 includes moveable sleeve 56. The catheter body 18 and anchor shaft 14 are substantially the same as in device 10; however, sleeve 56 extends completely around the diameter of the catheter body 18, so that the sleeve 56 can be slidably moved along the catheter body 18. In an alternative embodiment, not shown in the Figures, the moveable sleeve does not extend completely around the catheter body; rather it would cover only a portion of the diameter of, and be in slideable engagement with, the catheter body. The moveable sleeve can include a locking mechanism (not shown) for releasably securing the sleeve in different positions as desired by the physician.

In device 50, the locking and adjustment of the anchor shaft can be operated in an essentially identical manner as in device 10. However, additional control of loop 40 is afforded by adjusting the position of the moveable sleeve 56. FIG. 9A shows the device in the resting or unengaged position, with a suboptimal distal catheter curve, unable to intubate the relatively superior location of an unusually located coronary ostium 102. FIG. 9B shows the loop 40 abutting the contralateral cusp of aorta 100 with sleeve 56 positioned towards the distal end portion 22 of the catheter body 18. The catheter curve is tightened, allowing for coronary engagement. To increase the support, sleeve 56 can be moved toward the proximal end of the catheter body 18, to expose more of the distal portion 32 of the anchor shaft 14 and thus to enlarge the size of the loop 40. As shown in FIG. 9C, this movement causes the loop 40 to abut the contralateral wall and further enhance support for the catheter tip portion 22, driving it deeper into the coronary ostium 102.

Figure 7:
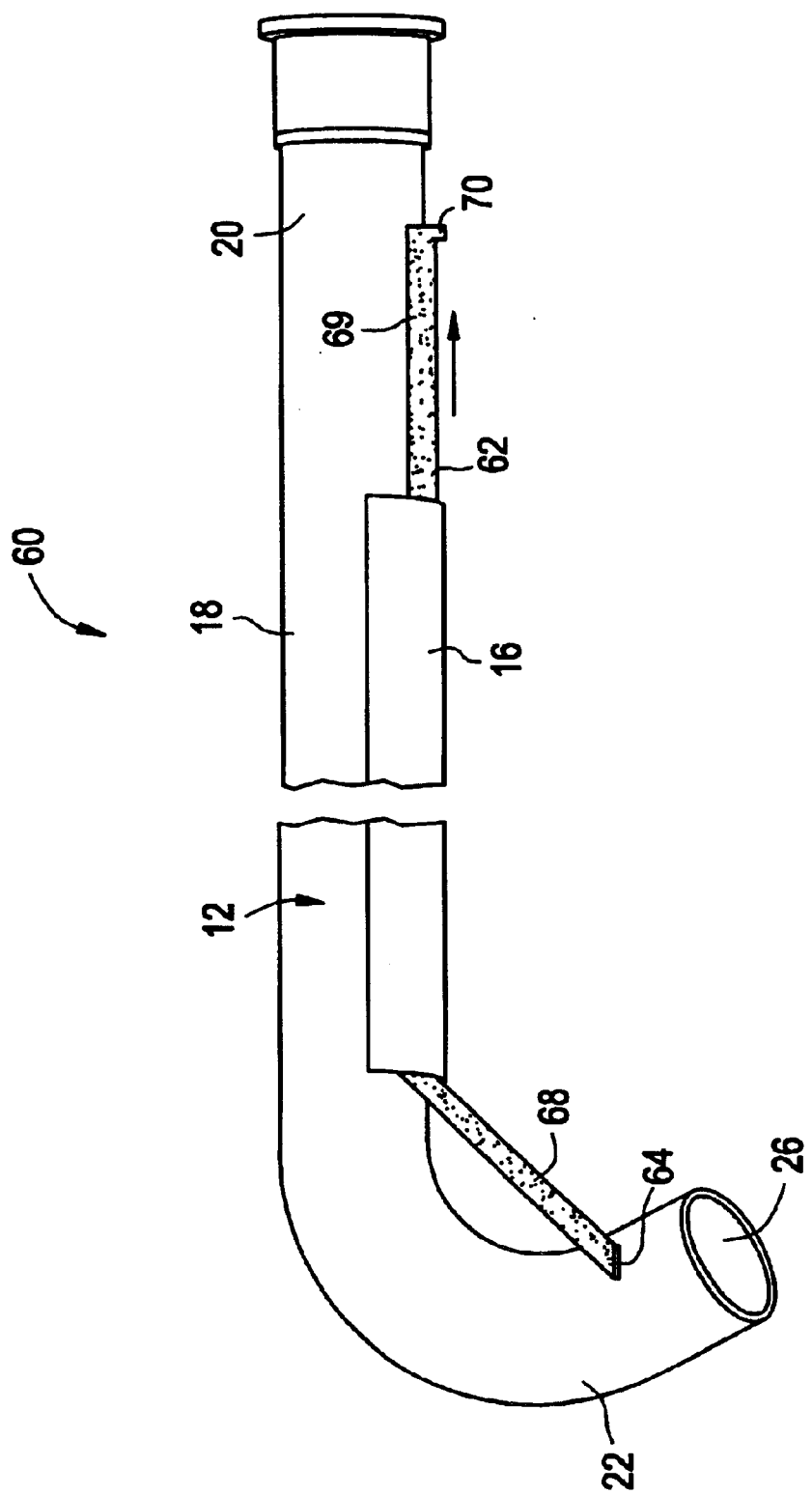
FIG. 7 is a perspective view of the catheter device of FIG. 6 with the anchor shaft in a retracted position.

A further useful embodiment is illustrated in FIGS. 6, 7, and 10. This catheter device includes an anchor shaft on the opposite side (inner curvature) of the catheter body to tighten the tip curvature as needed to allow fine manipulations for optimal coronary engagement, especially in unusual coronary locations.

As shown in FIGS. 6 and 7, the catheter device 60 includes catheter body 18, sleeve 16, and an anchor shaft 62 wherein the hinge point 64 is on the inner curvature of the distal portion 22 of the catheter body 18. (This is in contrast to device 10, where the hinge point is on the outer curvature.) The anchor shaft further includes proximal end portion 69, distal end portion 68, and locking means 70. In this embodiment, the anchor shaft may be referred to herein as a retraction anchor shaft, because the physician holding the proximal end of the anchor shaft retracts it proximally from its resting position in order to activate its curvature manipulation function. The anchor shaft 62 can be retracted to tighten the radius of curvature of the distal portion 22 of the catheter body 18, thereby providing additional operational versatility. For example, such an adjustment could convert a JR4 to a JR3 or Williams (3DRC) catheter. Anchor shaft 62 preferably is made of a softer material than the anchor shaft 14.

A further embodiment is illustrated in FIG. 12. The guiding catheter device 110, includes a catheter body 117 with a central lumen 118 extending between the proximal and distal ends, an extension anchor shaft 113 slidably positioned in a secondary lumen 112 formed by a sleeve 111 positioned on the outer curvature of the catheter body 117, and a retraction anchor shaft 116 slidably positioned in a tertiary lumen 115 formed by a sleeve 114 positioned on the inner curvature of the catheter body 117. The retraction anchor shaft 116 is located at a position which is substantially opposite the position of the extension anchor shaft 113 on the circumference of the catheter body 117. The retraction anchor shaft 116 can be retracted to tighten the radius of curvature of the distal portion 119 of the catheter body 117, thereby providing additional operational versatility. The extension anchor shaft 113 can be advanced distally along the secondary lumen 112, thereby causing the distal end portion 121 of the anchor shaft 113, as it exits from the secondary lumen 112, to bow or flex away from the catheter body 117 in the region between the hinge point 120 and the distal end of the sleeve 122. The loop that forms can be used to provide backup support for the distal tip 123 of the catheter and to facilitate greater control of the placement of the catheter tip. The retraction and extension anchor shafts can be operated concurrently or independently.

Figure 10B:
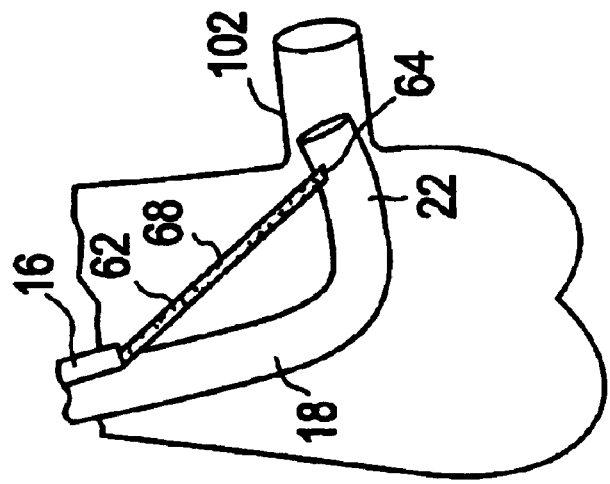
FIGS. 10A–B illustrate use of one embodiment of a catheter device with a retraction anchor shaft, shown located for use within an aorta in a resting position (FIG. 10A) and in a retracted position (FIG. 10B).
Figure 10A:
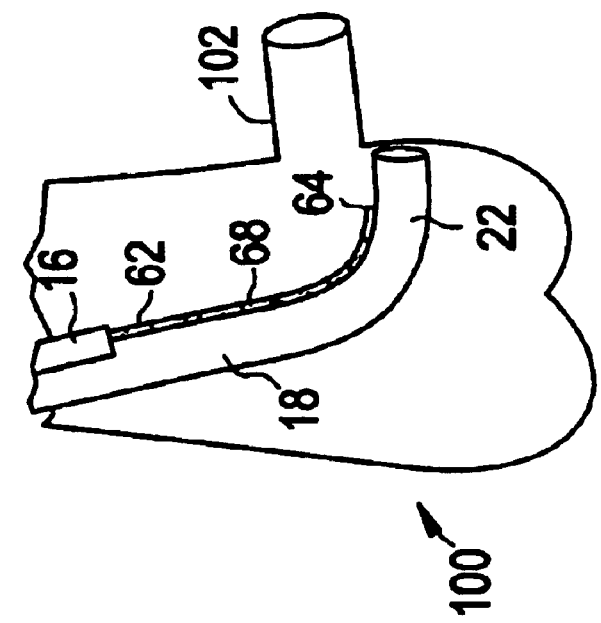

To operate device 60, the anchor shaft 62 is unlocked and then retracted in a proximal direction. Tension on the anchor shaft 62 cause the distal end portion 22 of the catheter body 18 to bend, decreasing the radius of curvature of distal end portion 22 between the distal end of the sleeve 16 and the hinge point 64. As shown in FIG. 10A, the tip of the catheter body, located in aorta 100, may be below the coronary ostium 102 when the anchor shaft 62 is in its zero or relaxed configuration. FIG. 10B shows the anchor shaft 62 that has been retracted, shortening the portion of distal end portion 68 of anchor shaft 62 between the distal end of the sleeve 16 and the hinge point 64, in an amount effective to redirect the tip of the catheter body into the coronary ostium 102.

Although not shown, the three embodiments described above can be used in any combination. For example, the catheter device could have two anchor shafts: one extension anchor shaft and one retraction anchor shaft. In addition, the movable sleeve could be used with an extension anchor shaft, a retraction anchor shaft, or with both.

The catheter devices described herein can be used in several different medical procedures. In preferred applications, they are used in cardiovascular system diagnosis and interventional cardiology. Preferably the catheter devices described herein are used to guide diagnostic contrast agents (e.g., for angiography) and therapeutic devices (e.g., stents, balloons, laser catheters, atherectomy catheters) into coronary arteries, for example for percutaneous transluminal coronary angioplasty. In one embodiment, a 6-Fr flexible catheter of the present design could be used for the diagnostic arteriogram, with varying degrees of backup support at the physician's disposal for the subsequent intervention.

Modifications and variations of the methods and devices described herein will be obvious to those skilled in the art from the foregoing detailed description. Such modifications and variations are intended to come within the scope of the appended claims.

I claim:

1. A versatile guiding catheter device comprising:
   a flexible catheter body having a proximal end, a distal end, and a central lumen open at both of the ends;
   a flexible sleeve having a proximal end and a distal end, the sleeve being secured to the catheter body so as to define a secondary lumen between the sleeve and the catheter body, and the distal end of the sleeve being secured to the catheter body at a position proximal the distal end of the catheter body; and
   an anchor shaft having a proximal end and a distal end, the anchor shaft extending through the secondary lumen, the distal end being fixedly attached to the catheter body between the distal end of the catheter body and the distal end of the sleeve to form a hinge point about which the distal position of the anchor shaft can rotate with respect to the catheter body;
   wherein the proximal end of the anchor shaft can be reversibly advanced toward the distal ends of the anchor shaft and catheter body to cause the distal end portion of the anchor shaft to bow away from the catheter body in the region between the hinge point and the distal end of the sleeve, forming a loop, said distal end of the sleeve remaining secured to the catheter body.

2. The guiding catheter device of claim 1, wherein the sleeve is moveably secured to the catheter body, so that the sleeve can be reversibly advanced toward the proximal ends of the anchor shaft and catheter body.

3. The guiding catheter device of claim 1, wherein the distal end portion of the catheter body is curved.

4. The guiding catheter device of claim 3, wherein the hinge point is located on the outer curvature of the curved distal end portion of the catheter body.

5. The guiding catheter device of claim 1, further comprises a retraction anchor shaft extending through a tertiary lumen defined between the sleeve and an outer surface area of the catheter body at a position which is substantially opposite the position of the first anchor shaft on the circumference of the catheter body.

6. The device of claim 1, wherein the anchor shaft comprises an elongated, incompressible ribbon.

7. The device of claim 6, wherein the ribbon has a width between about 20% and about 25% of the circumference of the catheter body.

8. The device of claim 6, wherein the ribbon is made of a synthetic polymer.

9. A versatile guiding catheter device comprising:
   a flexible catheter body having a proximal end, a distal end, and a central lumen extending therebetween;
   a flexible sleeve having a proximal end and a distal end, the sleeve being secured to the catheter body so as to define a secondary lumen between the sleeve and the catheter body, and the distal end of the sleeve being in a position proximal the distal end of the catheter body; and
   an anchor shaft having a proximal end and a distal end, the anchor shaft extending through the secondary lumen, the distal end being fixedly attached to the catheter body between the distal end of the catheter body and the distal end of the sleeve to form a hinge point about which the distal portion of the anchor shaft can rotate with respect to the catheter body, the proximal end portion of the anchor shaft comprising a locking means for securing the anchor shaft at one or more positions along the catheter body;
   wherein the proximal end of the anchor shaft can be reversibly advanced toward the distal ends of the anchor shaft and catheter body to cause the distal end portion of the anchor shaft to bow away from the catheter body in the region between the hinge point and the distal end of the sleeve, forming a loop.

10. The guiding catheter device of claim 9, wherein the locking means is selected from the group consisting of hook-and-loop fasteners, notch mechanisms, button-hole mechanisms, pressure sensitive adhesive materials, snaps, clips, clamps, and combinations thereof.

11. A versatile guiding catheter device comprising:
   a flexible catheter body having a proximal end, a distal end, and a central lumen extending therebetween;
   a flexible sleeve having a proximal end and a distal end, the sleeve being secured to the catheter body so as to define a secondary lumen between the sleeve and the catheter body, and the distal end of the sleeve being in a position proximal the distal end of the catheter body; and
   an anchor shaft having a proximal end and a distal end, the anchor shaft extending through the secondary lumen, the distal end being fixedly attached to the catheter body between the distal end of the catheter body and the distal end of the sleeve to form a hinge point about which the distal portion of the anchor shaft can rotate with respect to the catheter body;
   wherein the proximal end of the anchor shaft can be reversibly retracted away from the sleeve to cause the distal end of the anchor shaft to move toward the sleeve, decreasing the radius of curvature of the distal end portion of the catheter body.

12. The guiding catheter device of claim 11, wherein the sleeve is moveably secured to the catheter body, so that the sleeve can be reversibly advanced toward the proximal ends of the anchor shaft and catheter body.

13. The guiding catheter device of claim 11, wherein the distal end portion of the catheter body is curved in the absence of anchor shaft tension or compression.

14. The guiding catheter device of claim 13, wherein the hinge point is located on an inner curvature of the curved distal end portion of the catheter body.

15. The guiding catheter device of claim 11, wherein the proximal end portion of the anchor shaft comprises a locking means for securing the anchor shaft at one or more positions along the catheter body.

16. The guiding catheter device of claim 15, wherein the locking means is selected from the group consisting of hook-and-loop fasteners, notch mechanisms, button-hole mechanisms, pressure sensitive adhesive materials, snaps, clips, clamps, and combinations thereof.

17. A method for guiding a catheter into a coronary artery for coronary intervention, the method comprising:

providing a versatile guiding catheter device which comprises (i) a flexible catheter body having a proximal end, a distal end, and a central lumen open at both of the ends, (ii) a flexible sleeve having a proximal end and a distal end, the sleeve being secured to the catheter body so as to define a secondary lumen between the sleeve and the catheter body, and the distal end of the sleeve being secured to the catheter body at a position proximal the distal end of the catheter body, and (iii) an anchor shaft having a proximal end and a distal end, the anchor shaft extending through the secondary lumen, the distal end being fixedly attached to the catheter body between the distal end of the catheter body and the distal end of the sleeve to form a hinge point about which the distal portion of the anchor shaft can be rotated with respect to the catheter body;

inserting into the aorta of a patient in need of coronary intervention the distal ends of the catheter body, sleeve, and anchor shaft, with the distal end portion of the anchor shaft in a resting position adjacent the catheter body;

advancing the proximal end of the anchor shaft toward the distal ends of the anchor shaft and catheter body to cause the distal end portion of the anchor shaft to bow away from the catheter body in the region between the hinge point and the distal end of the sleeve, forming a loop which is defined by the portions of the anchor shaft and catheter body that are between the distal end of the sleeve and the hinge point, said distal end of the sleeve remaining secured to the catheter body; and adjusting the position of the proximal end of the anchor shaft to cause the loop to engage an interior surface of the aorta in manner effective to facilitate insertion of the distal end of the catheter body into a coronary ostium, to provide backup support for maintaining a position of the distal end of the catheter body within a coronary ostium, or both.

18. The method of claim 17, wherein the sleeve is moveably secured to the catheter body, and the method further comprises retracting the sleeve toward the proximal ends of the anchor shaft and catheter body to enlarge the loop.

19. The method of claim 17, wherein the distal end of the catheter body comprises a curved portion, and the anchor shaft and the hinge point are along the outer curvature of the curved portion.

20. A method for guiding a catheter into a coronary artery for coronary intervention, the method comprising:

providing a versatile guiding catheter device which comprises (i) a flexible catheter body having a proximal end, a distal end, and a central lumen extending therebetween, (ii) a flexible sleeve having a proximal end and a distal end, the sleeve being secured to the catheter body so as to define a secondary lumen between the sleeve and the catheter body, and (iii) an anchor shaft having a proximal end and a distal end, the anchor shaft extending through the secondary lumen, the distal end being fixedly attached to the catheter body at an outer surface area between the distal end of the catheter body and the distal end of the sleeve to form a hinge point about which the distal portion of the anchor shaft can be rotated with respect to the catheter body;

inserting into the aorta of a patient in need of coronary intervention the distal ends of the catheter body, sleeve, and anchor shaft, with the distal end portion of the anchor shaft in a resting position adjacent the catheter body;

retracting the proximal end of the anchor shaft away from the sleeve to cause the distal end of the anchor shaft to move toward the sleeve, decreasing the radius of curvature of the distal end portion of the catheter body; and adjusting the position of the proximal end of the anchor shaft to cause the loop to facilitate insertion of the distal end of the catheter body into a coronary ostium.

21. The method of claim 20, wherein the distal end of the catheter body comprises a curved portion, and the anchor shaft and the hinge point are along the inner curvature of the curved portion.

22. A versatile guiding catheter device comprising:

a flexible catheter body having a proximal end, a distal end, and a central lumen open at both of the ends;

a flexible sleeve having a proximal end and a distal end, the sleeve being secured to the catheter body so as to define a secondary lumen between the sleeve and the catheter body, and the distal end of the sleeve being in a position proximal the distal end of the catheter body; and an anchor shaft having a proximal end and a distal end, the anchor shaft extending through the secondary lumen, the distal end being fixedly attached to the catheter body between the distal end of the catheter body and the distal end of the sleeve to form a hinge point about which the distal portion of the anchor shaft can rotate with respect to the catheter body;

wherein the sleeve is moveably secured to the catheter body, so that the sleeve can be reversibly advanced toward the proximal ends of the anchor shaft and catheter body; and wherein the proximal end of the anchor shaft can be reversibly advanced toward the distal ends of the anchor shaft and catheter body to cause the distal end portion of the anchor shaft to bow away from the catheter body in the region between the hinge point and the distal end of the sleeve, forming a loop.

23. A versatile guiding catheter device comprising:

a flexible catheter body having a proximal end, a distal end, and a central lumen open at both of the ends;

a flexible sleeve having a proximal end and a distal end, the sleeve being secured to the catheter body wherein the sleeve and the catheter body define a secondary lumen, and the distal end of the sleeve positioned proximal the distal end of the catheter body; and an anchor shaft having a proximal end and a distal end, the anchor shaft extending through the secondary lumen, the distal end being fixedly attached to the catheter body between the distal end of the catheter body and the distal end of the sleeve to form a hinge point about which the distal portion of the anchor shaft can rotate with respect to the catheter body;

wherein the proximal end of the anchor shaft can be reversibly advanced toward the distal ends of the anchor shaft and catheter body to cause the distal end portion of the anchor shaft to bow away from the catheter body in the region between the hinge point and the distal end of the sleeve, forming a loop.

* * * * *